United States Patent
Desai et al.

(10) Patent No.: US 9,878,137 B2
(45) Date of Patent: Jan. 30, 2018

(54) BIOACTIVE AGENT DELIVERY DEVICES AND METHODS OF MAKING AND USING THE SAME

(71) Applicant: The Regents of the University of California, Oakland, CA (US)

(72) Inventors: Tejal A Desai, San Francisco, CA (US); Hariharasudhan D. Chirra, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 193 days.

(21) Appl. No.: 14/403,056

(22) PCT Filed: May 24, 2013

(86) PCT No.: PCT/US2013/042710
§ 371 (c)(1),
(2) Date: Nov. 21, 2014

(87) PCT Pub. No.: WO2013/181107
PCT Pub. Date: Dec. 5, 2013

(65) Prior Publication Data
US 2015/0119807 A1    Apr. 30, 2015

Related U.S. Application Data

(60) Provisional application No. 61/653,119, filed on May 30, 2012.

(51) Int. Cl.
| G03F 1/80 | (2012.01) |
| A61M 31/00 | (2006.01) |
| G03F 7/00 | (2006.01) |
| G03F 7/40 | (2006.01) |
| A61K 9/00 | (2006.01) |

(52) U.S. Cl.
CPC ......... *A61M 31/002* (2013.01); *A61K 9/0097* (2013.01); *G03F 7/0035* (2013.01); *G03F 7/40* (2013.01)

(58) Field of Classification Search
CPC .................................................. A61K 9/0097
USPC .................................................. 430/316, 314
See application file for complete search history.

(56) References Cited

U.S. PATENT DOCUMENTS

| 5,410,016 A | 4/1995 | Hubbell et al. |
| 5,567,271 A | 10/1996 | Chu et al. |
| 5,797,898 A | 8/1998 | Santini et al. |
| 6,355,270 B1 | 3/2002 | Ferrari et al. |
| 6,669,807 B2 | 12/2003 | Nakatani |
| 6,770,441 B2 | 8/2004 | Dickinson et al. |
| 7,622,081 B2 | 11/2009 | Chou et al. |
| 2002/0099359 A1 | 7/2002 | Santini et al. |
| 2002/0115224 A1 | 8/2002 | Rudel et al. |
| 2005/0169962 A1 | 8/2005 | Bhatia et al. |
| 2006/0093646 A1 | 5/2006 | Cima et al. |
| 2008/0039792 A1 | 2/2008 | Meng et al. |
| 2010/0278931 A1 | 11/2010 | Ashton et al. |
| 2010/0318193 A1 | 12/2010 | Desai et al. |
| 2012/0114734 A1 | 5/2012 | Desai et al. |

FOREIGN PATENT DOCUMENTS

| WO | 2000/41740 | 7/2000 |
| WO | 2004/006840 | 1/2004 |

OTHER PUBLICATIONS

Ainslie and Desai (2008) "Microfabricated implants for applications in therapeutic delivery, tissue engineering, and biosensing" Lab on a Chip 8:1864-1878.
Bugarski et al. (1994) "Electrostatic droplet generation: Mechanism of polymer droplet formation" AIChE J 40(6): 1026-1031.
Chirra and Hilt (2010) "Nanoscale Characterization of the Equilibrium and Kinetic Response of Hydrogel Structures" Langmuir 26(13):11249-11257.
Fischer et al. (2009) "Biomimetic Nanowire Coatings for Next Generation Adhesive Drug Delivery Systems" Nano Lett 9(2):716-720.
Grayson et al. (2003) "Multi-pulse drug delivery from a resorbable polymeric microchip device" Nat Mater 2:767-772.
Grayson et al. (2004) "Molecular release from a polymeric microreservoir device: Influence of chemistry, polymer swelling, and loading on device performance" J Biomed Mater Res Part A 69A(3):502-512.
Kitchens et al. (2006) "Transport of Poly(Amidoamine) Dendrimers across Caco-2 Cell Monolayers: Influence of Size, Charge and Fluorescent Labeling" Pharm Res 33(12):2818-2826.
Lai et al. (2007) "Privileged delivery of polymer nanoparticles to the perinuclear region of live cells via a non-clathrin, non-degradative pathway" Biomaterials 28(18):2876-2884.
Leach et al. (2005) "Encapsulation of protein nanoparticles into uniform-sized microspheres formed in a spinning oil film" AAPS PharmSciTech 6(4):E605-E617.
Lehr et al. (1992) "In vitro evaluation of mucoadhesive properties of chitosan and some other natural polymers" Int J Pharm 78(1-3):43-48.
Randall et al. (2007) "3D lithographically fabricated nanoliter containers for drug delivery" Adv Drug Deliv Rev 59 (15):1547-1561.
Rejman et al. (2004) "Size-dependent internalization of particles via the pathways of clathrin- and caveolae—mediated endocytosis" Biochem. J 377:159-169.
Uskokovic et al. (2012) "PEGylated silicon nanowire coated silica microparticles for drug delivery across intestinal epithelium" Biomaterials 33(5):1663-1672.
Wolters et al. (1992) "A versatile alginate droplet generator applicable for microencapsulation of pancreatic islets" J Appl Biomater 3(4):281-286.
Ishihara (2004) "Nano Bio Engineering Material" Frontier Publishing Company, pp. 23-25.

*Primary Examiner* — Daborah Chacko Davis
(74) *Attorney, Agent, or Firm* — Edward J. Baba; Shweta Chandra; Bozicevic, Field & Francis LLP

(57) ABSTRACT

A method of preparing a substantially planar microdevice comprising a plurality of reservoirs is provided. In general, the method comprises forming a plurality of microdevices comprising a plurality of reservoirs from a planar layer of a biocompatible polymer. The method also comprises depositing one or more bioactive agents into the reservoirs. The microdevice is configured to attach to a target tissue and release the bioactive agent in close proximity to the tissue.

19 Claims, 8 Drawing Sheets

BIOACTIVE AGENT DELIVERY DEVICES AND METHODS OF MAKING AND USING THE SAME

CROSS-REFERENCE TO RELATED APPLICATIONS

This application is a national phase patent application of PCT/US2013/042710, filed on May 24, 2013, which claims priority benefit to the filing date of U.S. Provisional Patent Application Ser. No. 61/653,119, filed on May 30, 2012, the disclosure of which application is herein incorporated by reference in its entirety.

INTRODUCTION

Among the various conventional modes of drug administration, oral delivery of pharmaceuticals is a preferred route as it offers several advantages. It is less invasive, provides higher patient compliance, rapid availability, and low cost of manufacturing. However, a unique set of intestinal barriers including the stomach's acidic environment, poor permeation of active therapeutics across the thick mucus and epithelial interface, an array of drug degrading intestinal enzymes, and limited retention time due to peristalsis and shear flow conditions limit the overall drug efficacy. There are also instances where a combination therapy is needed, where multiple drugs are to be delivered at the same time to achieve a synergistic effect. In addition, the absence of targeting strategies for intestinal diseases such as, irritable bowel syndrome (IBS), inflammatory bowel disease (IBD), and Crohn's disease results in an increased risk of side effects.

Although various oral delivery systems including enteric-coated capsules, tablets, particles, liposomes, bioadhesive agents, and permeation enhancers have been developed in an effort to improve oral bioavailability of drugs, many of these systems suffer from poor intestinal localization and low therapeutic efficacy due to the various physiological conditions inside the intestine and high shear fluid flow. As such, these systems require administration with increased frequency and over an extended time period, which is not practical for expensive and/or toxic drugs.

Microfabricated drug delivery vehicles, such as, microparticles have been developed by techniques such as, emulsification, droplet extrusion, solvent evaporation, or nano-precipitation. However, these microparticles tend to aggregate leading to polydispersity (B. Bugarski, et al., AIChE J. 40 (1994), 1026-1031; G. H. J. Wolters, et al., J. Appl. Biomater. 3 (1992), 281-286; W. T. Leach, et al., AAPS Pharm. Sci. Tech. 6 (2005), E605-E617). The polydispersity of these microparticles can lead to non-uniform drug loading and release (S. K. Lai, et al., Biomaterials. 28 (2007), 2876-2884; J. Rejman, et al., Biochem. J. 377 (2004), 159-169; C. L. Randall, et al., Adv. Drug Deliv. Rev. 59 (2007), 1547-1561). Moreover, the symmetry of spherical particles can result in a loss of drug into the lumen caused by the omni-directional drug release at the mucus-particle interface (K. M. Ainslie and T. A. Desai, Lab Chip. 8 (2008), 1864-1878).

As such, there is a need for devices for delivery of a bioactive agent(s) to a target tissue. The invention described herein fulfills this need, as well as other.

SUMMARY OF THE INVENTION

A method of preparing a substantially planar microdevice comprising a plurality of reservoirs is provided. In general, the method comprises forming a plurality of microdevices comprising a plurality of reservoirs from a planar layer of a biocompatible polymer. The method also comprises depositing one or more bioactive agents into the reservoirs. The microdevice is configured to attach to a target tissue and release the bioactive agent in close proximity to the tissue. Accordingly, the microdevice is configured to release the bioactive agent unidirectionally.

In certain embodiments, the method of preparing a substantially planar microdevice comprising a plurality of reservoirs includes fabricating a planar layer of a biocompatible polymer on a substrate, the planar layer comprising a first surface and a second surface opposite to the first surface; defining a microdevice structure in the planar layer using successive deposition of photoresist layer, light exposure, and etching; and introducing a plurality of reservoirs in the microdevice structure using successive deposition of photoresist layer, light exposure, and partial etching, wherein the plurality of reservoirs are open only at a first surface of the microdevice and are closed at the second surface of the microdevice, thereby producing a planar microdevice comprising a plurality of reservoirs.

In certain cases, the method further comprises depositing a bioactive agent into the plurality of reservoirs. The bioactive agent may be deposited in the form of solution comprising the bioactive agent and a photopolymer, wherein the method further comprises exposing the reservoirs to light, thereby polymerizing the solution.

In certain cases, the method includes depositing a first solution comprising a first bioactive agent into the plurality of reservoirs; polymerizing the first solution only in the first reservoir of the plurality of reservoirs; removing unpolymerized first solution; depositing a second solution comprising a second bioactive agent into the plurality of reservoirs and polymerizing the second solution only in a second reservoir of the plurality of reservoirs. In certain embodiments, the first solution may also include a prepolymer, for example, a photopolymer, and polymerizing the first solution only in the first reservoir may include exposing only the first reservoir to light. In certain embodiments, the second solution may also include a prepolymer, for example, a photopolymer, and polymerizing the second solution only in the second reservoir may include exposing only the second reservoir to light.

In certain embodiments, the first solution may comprise a first prepolymer and the second solution may comprise a second prepolymer, wherein the first bioactive agent is released from the first reservoir at a different rate compared to release of the second bioactive agent from the second reservoir.

In certain embodiments, the method includes, after the microdevice structure has been defined, a step of attaching an adhesion molecule to the first surface to facilitate attachment of the first surface of the microdevice to cells of a target tissue.

In certain embodiments, the method includes a step of attaching an adhesion molecule to the first surface to facilitate attachment of the first surface of the microdevice to cells of a target tissue, after the plurality of reservoirs in the microdevice structure has been introduced.

In some cases, the biocompatible polymer may be poly (DL-lactide-co-glycolide) (PLGA), poly(DL-lactide-co-ε-caprolactone) (DLPLCL), poly(ε-caprolactone) (PCL), collogen, gelatin, agarose, poly(methyl methacrylate), galatin/ε-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In certain cases, the biocompatible polymer may be poly(methyl methacrylate) or a derivative thereof. In other embodiments, the biocompatible polymer may be poly(ε-caprolactone) (PCL) or a derivative thereof.

In certain embodiments, fabricating the substantially planar layer includes depositing the biocompatible polymer at an average thickness of about 5 µm to about 100 µm.

In certain examples, the microdevice may have an average thickness of about 5 µm to about 100 µm.

In certain embodiments, the microdevice may be disc-shaped, which may be circular or oval in shape. In some embodiments, the microdevice has an average diameter of about 50 µm-1000 µm.

In some cases, the plurality of reservoirs may have different depths. In other cases, the plurality of reservoirs may have the same or similar depths. In some embodiments, the plurality of reservoirs may have different volumes. In some embodiments, the plurality of reservoirs may have different diameters.

In exemplary embodiments, the method may further comprise removing the microdevice from the substrate.

In certain cases, the cell adhesion molecule is lectin, chitosan, laminin, fibrin, fibronectin, proteoglycans, glycoproteins, glycosaminoglycan, or a combination thereof.

The microdevice may be useful as medical implants, including gastrointestinal implants, dental implants, cardiovascular implants, neurological implants, neurovascular implants, muscular implants, and ocular implants. The present invention also provides methods of treating a patient in need of such an implant.

As noted above, the microdevice includes a bioactive agent(s) for elution of the bioactive agent from a single surface of the microdevice to the adjacent tissue upon placement in a subject. In some embodiments, the microdevice attaches to a mucosal surface and provides a localized delivery of the bioactive agent to the mucosal surface.

In some embodiments, the bioactive agent is selected from a polypeptide, growth factor, a steroid, an antibody, an antibody fragment, a DNA, an RNA, and siRNA, an antimicrobial agent, an antibiotic, an antiretroviral drug, an anti-inflammatory compound, an antitumor agent, anti-angiogeneic agent, and a chemotherapeutic agent.

A microdevice produced by the process outlined above is also described herein.

These and other objects, advantages, and features of the invention will become apparent to those persons skilled in the art upon reading the details of the invention as more fully described below.

BRIEF DESCRIPTION OF THE DRAWINGS

A detailed description of various embodiments of the present disclosure is provided herein with reference to the accompanying drawings, which are briefly described below. The drawings are illustrative. It is emphasized that, according to common practice, the various features of the drawings are not to-scale. On the contrary, the dimensions of the various features are arbitrarily expanded or reduced for clarity. The drawings illustrate various embodiments of the present disclosure and may illustrate one or more embodiment(s) or example(s) of the present disclosure in whole or in part.

FIG. 1, Panel B is a scanning electron microscopic (SEM) image of the fabricated microdevice. FIG. 1, Panel C depicts the dimensions of the microdevice.

FIG. 2, Panel B, shows a fluorescent micrograph showing the presence of a single model drug in all three reservoirs of the same microdevice. FIG. 2, Panel C, shows a fluorescent micrograph composite of multi-drug loaded microdevices.

DETAILED DESCRIPTION OF THE INVENTION

Figure 1:
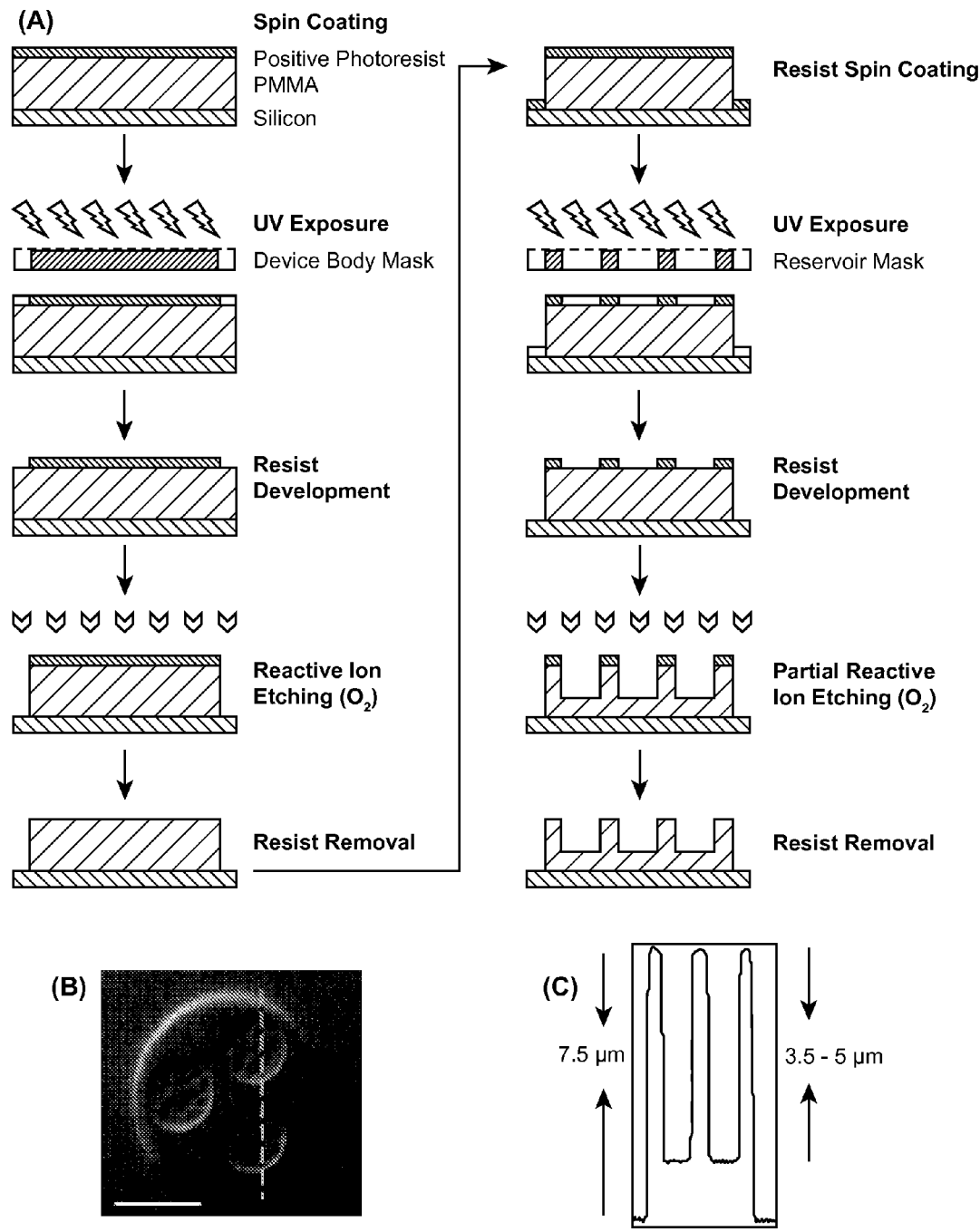
FIG. 1, Panel A provides a schematic of fabrication process of a microdevice.

A method of preparing a substantially planar microdevice comprising a plurality of reservoirs is provided. In general, the method comprises forming a plurality of microdevices containing a plurality of reservoirs from a planar layer of a biocompatible polymer. The method also comprises depositing one or more bioactive agents into the reservoirs. The microdevice is configured to attach to a target tissue and release the bioactive agent into the tissue. Accordingly, the microdevice is configured to release the bioactive agent unidirectionally.

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a microdevice" includes a plurality of such microdevices and reference to "the bioactive agent" includes reference to one or more bioactive agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Microdevices and Methods for Making the Same

As noted above, the present invention provides microdevices that are generally planar and include a plurality of reservoirs in which a bioactive agent may be placed. These microdevices can contain a single bioactive agent in the plurality of reservoirs, a mixture of two or more bioactive agents in the plurality of reservoirs, or different bioactive agents in separate reservoirs. In addition, the microdevices may be configured to release bioactive agents present in different reservoirs at different rates. The microdevices may further include an adhesion molecule on a first surface of the microdevice. The adhesion molecule may facilitate attachment of the first surface of the microdevice to cells of a target tissue resulting in release of the bioactive agent from the reservoirs towards the cells.

The substantially planar microdevice comprising a plurality of reservoirs may be prepared by depositing a planar layer of a biocompatible polymer on a substrate. The planar layer is substantially flat and includes a first surface and a second surface opposite to the first surface, where the second surface is in contact with the substrate. A plurality of microdevice structures may be defined in the planar layer using photolithography and etching. In general, the method may include depositing a layer of a photoresist on the first surface of the planar layer, exposing a defined region of the photoresist to light, and etching areas of the polymer layer from which the photoresist has been removed to remove the polymer, thereby providing a plurality of microdevice structures. As used herein, the phrase "microdevice structure" refers to an unfinished microdevice, wherein the unfinished microdevices do not yet have reservoirs defined in the microdevice structure.

A plurality of reservoirs may be introduced in the microdevice structures using photolithography and partial etching. In general, the method may include depositing a layer of a photoresist on a first surface of the microdevice structures. The first surface of the microdevice structure corresponds to the first surface of the planar polymer layer. Defined regions of the photoresist may then be removed by exposure to light. The regions of polymer from which the photoresist has been removed may then be partially etched to remove the polymer. As used herein, "partial etching" as contrasted with "etching" or "complete etching" refers to removing the polymer partially, for example, in embodiments where the microdevice structure is, for example, 10 μm thick, partial etching removes the polymer to a depth of less than 10 μm, such as, a depth of 1 μm, 2 μm, 3 μm, 4 μm, 5 μm, 6 μm, 7 μm, 8 μm, or 9 μm. In contrast, "complete etching" or "etching" as used herein refers to removing the polymer completely or substantially completely, for example, in embodiments where the planar layer of biocompatible material is, for example, 10 μm thick, "etching" or "complete etching" removes the polymer to a depth of about 10 μm, such as, a depth of 9.999 μm, 9.5 μm, 9.2 μm. In general, "etching" or "complete etching" removes the polymer to an extent such that the individual microdevices fabricated on a substrate are no longer connected to each other as a result of the polymer present in between the microdevices not being completely removed. As such, "etching" or "complete etching" provides for microdevices that when removed from the substrate are released as individual microdevices instead of being connected by residual polymer layer.

The plurality of microdevices with the plurality of reservoirs may then be loaded with bioactive agent(s). In general, the depositing of bioactive agent(s) in the microdevices is carried out while the microdevices are attached to the substrate. In general, the bioactive agent is loaded into the reservoirs in conjunction with a prepolymer. As used herein, the phrase "in conjunction with" in the context of a prepolymer refers to filling of the bioactive agent mixed with a prepolymer into the reservoirs, or loading the bioactive agent into reservoirs which already contain a prepolymer, or filling the bioactive agent into reservoirs followed by filling the reservoirs with a prepolymer. In certain instances, the bioactive agent may be in a solution containing a prepolymer and the solution may then be deposited into the reservoirs.

Following deposition of the bioactive agent into the reservoirs in conjunction with a prepolymer, the prepolymer may be polymerized in one or more of the reservoirs. In certain embodiments, one or more bioactive agents may be deposited in the reservoirs. In other embodiments, a first bioactive agent may be deposited into a first reservoir or a plurality of first reservoirs and second bioactive agent may be deposited into a second reservoir or a plurality of second reservoirs of the microdevices. In other embodiments, a first bioactive agent may be deposited into a first reservoir, a second bioactive agent may be deposited into a second reservoir, a third bioactive agent may be deposited into a third reservoir, and so on.

As noted above, the bioactive agent(s) may be deposited into the reservoirs in conjunction with a prepolymer. The preolymer may be polymerized by a variety of techniques, such as, exposure to light, heating, drying, and the like.

In certain embodiments, a first solution comprising a first bioactive agent and a first prepolymer may be deposited into a first reservoir of the plurality of microdevices. In certain embodiments, the depositing of the first solution comprises depositing the first solution onto the first surface of the microdevice resulting in filling of the plurality of reservoirs with the first solution. The first solution may then be polymerized only in the first reservoir in the plurality of microdevices. Any unpolymerized first solution deposited on the microdevice and/or in the reservoirs may then be removed. The method may further include depositing a second solution comprising a second bioactive agent and a second prepolymer into a second reservoir of the plurality of microdevices. In certain instances, the depositing of the second solution comprises depositing the second solution onto the first surface of the microdevice resulting in filling of any empty reservoirs with the second solution. The second solution may then be polymerized only in the second reservoir in the plurality of microdevices. The process may be repeated to deposit a third bioactive agent, a fourth bioactive agent, and so forth.

In certain embodiments, the first, second, third, fourth bioactive agents may be different bioactive agents, where the different bioactive agents are released simultaneously or sequentially. In certain embodiments, the same prepolymer may be used for loading the different bioactive agents. In other cases, different prepolymers may be used for loading the different bioactive agents. Accordingly, the first, second, third prepolymer may be the same prepolymer or different prepolymers.

A variety of prepolymers known in the art may be used. In certain embodiments, the prepolymer may be mixed with a photoinitiator, wherein exposure of the photoinitiator to light results in polymerization of the prepolymer. Useful photoinitiators can be those known in the art, such as, those disclosed in U.S. Pat. No. 5,410,016. For example, the photoinitiator may be acetophenone derivatives, e.g., dimethyl acetophenone (DMPA), 2-methoxy-2-phenylacetophenone, 2,2-dimethoxy-2-phenyl acetophenone; ethyl eosin; camphorquinone. Initiation of polymerization may be accomplished by irradiation with light at a wavelength of between about 200-700 nm, for example, 100 nm-440 nm.

In other embodiments, thermal polymerization initiator systems may also be used to selectively polymerize a bioactive agent containing solution in a particular reservoir. Such systems include, for example, potassium persulfate, with or without tetraamethyl ethylenediamine; benzoylperoxide, with or without triethanolamine; and ammonium persulfate with sodium bisulfite.

In certain cases, one or more adhesion molecules may be deposited on the first surface of the microdevice structure before the defining of reservoirs in the microdevice structures. In other cases, one or more adhesion molecules may be deposited on the first surface of the microdevice after the defining of reservoirs in the microdevice structures. In certain cases, one or more adhesion molecules may be deposited on the first surface of the microdevice after depositing a bioactive agent in the reservoir(s) of the microdevices.

The finished microdevice may be removed from the substrate using standard procedures to provide a plurality of individual microdevices. In general, the microdevices released from the substrate are released as individual microdevices such that the microdevices are not interconnected by any residual polymer layer. In certain cases, removing the microdevice from the substrate results in release of microdevices wherein more than 50% of the microdevices are released as single microdevices, for example, more than 60%, 70%, 80%, 90%, or more of the microdevices are released as single microdevices.

Any substrate suitable for carrying out the subsequent steps of the method may be used for depositing a layer of biocompatible polymer. In certain examples, the substrate is a silicon wafer, a glass chip, a plastic chip, or another suitable material. The substrate may be of any size, shape, and dimension. The size of the substrate may be selected based on, for example, the number of microdevices to be manufactured. In certain cases, the substrate is a silicon wafer. In certain cases, the silicon wafer is a 1-inch silicon wafer, or a 2-inch silicon wafer, or a 3-inch silicon wafer, or a 4-inch silicon wafer, or a 6-inch silicon wafer, or a 12-inch silicon wafer.

The planar layer of a biocompatible polymer may be deposited on the substrate using a variety of deposition techniques. In certain cases, the biocompatible polymer may be deposited by coating the polymer in form of a solution onto the substrate. Coating may be carried out by dipping the substrate in the polymer solution, by pipetting the polymer solution onto the substrate, or by spin coating, for example. The solvent in the polymer solution may be subsequently dried to obtain the planar layer of the biocompatible polymer. Drying may include air drying, forced air drying, heating, such as, baking, a combination thereof, and the like.

The planar layer biocompatible polymer is substantially uniform in thickness and the average thickness may range from 5 µm to about 100 µm. For example, the planar layer may have an average thickness of about 5 µm, 8 µm, 10 µm, 12 µm, 15 µm, 30 µm, 40 µm, 50 µm, 60 µm, 70 µm, 80 µm, 90 µm, or 100 µm.

The biocompatible polymer may be poly(DL-lactide-co-glycolide) (PLGA), poly(DL-lactide-co-ε-caprolactone) (DLPLCL), poly(ε-caprolactone) (PCL), collogen, gelatin, agarose, poly(methyl methacrylate), galatin/ε-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In certain cases, the biocompatible polymer may be poly(methyl methacrylate) or a derivative thereof. In other embodiments, the biocompatible polymer may be poly(ε-caprolactone) (PCL) or a derivative thereof.

Either a positive or a negative photoresist may be used to define the dimensions and shape of the microdevice structures. The photoresist may be deposited by dipping the substrate with the polymer layer in a solution containing the photoresist, by pipetting the photoresist solution onto the substrate, or by spin coating, for example. In certain cases, a positive photoresist may be used. A mask that defines the shape and surface area of the microdevice structures may be positioned over the photoresist. In certain embodiments, the mask may allow light to pass through a ring shaped region in the mask, thereby exposing a ring shaped region of the positive photoresist to light and making the photoresist in the ring shaped region soluble to the photoresist developer. Accordingly, upon development of the photoresist, ring shaped region of the photoresist is removed.

In other embodiments, the photoresist may be a negative photoresist. In these embodiments, the mask may be designed to allow light to pass through a circular region in the mask, thereby exposing a circular region of the negative photoresist to light and making the photoresist in the ring shaped region surrounding the circular region soluble to the photoresist developer. Accordingly, upon development of the photoresist, a ring shaped region of the photoresist is removed.

A variety of positive and negative photoresists may be used in the methods disclosed herein. As used herein, the phrase "positive photoresist" refers to a type of photoresist in which the portion of the photoresist that is exposed to light becomes soluble to the photoresist developer. While, the portion of the photoresist that is unexposed remains insoluble to the photoresist developer. As used herein, the phrase "negative photoresist" refers to a type of photoresist in which the portion of the photoresist that is exposed to light becomes insoluble to the photoresist developer. While, the unexposed portion of the photoresist is dissolved by the photoresist developer. For example, the photoresist may be Hoechst AZ 4620, Hoechst AZ 4562, AZ 1500, e.g., AZ 1514 H, Shipley 1400-17, Shipley 1400-27, Shipley 1400-37, etc.

Other shapes of the microdevice structures, such as triangular, oval, diamond, etc., may also be defined by using an appropriately designed mask. The surface area of the microdevice may be determined by the surface area of the area in the photomask through which the light passes. As such, the surface area of the microdevice may be in the range of 1,900 $\mu m^2$-790,000 $\mu m^2$, such as 3,000 $\mu m^2$-500,000 $\mu m^2$, or about 10,000 $\mu m^2$-100,000 $\mu m^2$, or about 15,000 $\mu m^2$-50,000 $\mu m^2$, or about 20,000 $\mu m^2$-40,000 $\mu m^2$, e.g., 18,000 $\mu m^2$-35,000 $\mu m^2$, for example, about 15,000 $\mu m^2$, 17,000 $\mu m^2$, 19,000 $\mu m^2$, 20,000 $\mu m^2$, or about 23,000 $\mu m^2$. In certain cases, the microdevice may be circular in shape and have an average diameter in the range of about 50 $\mu m$-1000 $\mu m$, for example, 70 $\mu m$-500 $\mu m$, 80 $\mu m$-300 $\mu m$, 90 $\mu m$-250 $\mu m$, 100 $\mu m$-200 $\mu m$, e.g., 50 $\mu m$, 60 $\mu m$, 70 $\mu m$, 80 $\mu m$, 90 $\mu m$, 100 $\mu m$, 130 $\mu m$, 150 $\mu m$, 180 $\mu m$, 200 $\mu m$, 250 $\mu m$, 300 $\mu m$, 400 $\mu m$, or 500 $\mu m$.

The photomask may be generated by standard procedure based on the desired pattern of the microdevices to be manufactured. As described above, the image for the photomask defines the shape and dimension of the microdevices.

Light may be used to expose a defined region of the photoresist layer via the mask. In certain cases, light may be a short wavelength light (for example, a wavelength of about 100 nm-440 nm), such as, ultra violet (UV) light, deep UV light, H and I lines of a mercury-vapor lamp. The step of exposing the photoresist to light may be followed with a step of photoresist development where the photoresist is contacted with a photoresist developer. In embodiments, where a positive photoresist is used, the regions of the positive photoresist layer exposed to light are washed away in the photoresist developer. In embodiments, where a negative photoresist is used, the regions of the negative photoresist layer not exposed to light are washed away in the photoresist developer.

Any standard photoresist developer compatible with the photoresist deposited may be used in the methods described herein. As such, a positive developer may be used to remove any positive photoresist exposed to light. In certain cases, a negative developer may be used to remove any negative photoresist not exposed to light.

The regions of the polymer layer from which the photoresist has been removed are then etched to remove the biocompatible polymer layer. The portion or portions of the biocompatible polymer layer that are covered by the photoresist form the microdevice. A dry or wet etching process as is standard in the art may be used to remove the exposed biocompatible polymer layer. In certain cases, the etching process is reactive ion etching. Standard procedures and apparatus for etching may be used. For example, reactive ion etching methods and apparatus are described in U.S. Pat. Nos. 6,669,807, 5,567,271, which are herein incorporated by reference. The etching is carried out for a length of time sufficient to remove all of the polymer material not covered with the photoresist such that the plurality of microdevice structures are not connected together via any residual polymer material.

Following the etching step, the photoresist may be removed using any standard photoresist remover or photoresist stripper compatible with the photoresist used. Exemplary photoresist removers include 1-methyl-2-pyrrolidon, dimethyl sulfoxide, AZ® 100 Remover, and the like.

The plurality of microdevice structures generated by the foregoing method may be 2, 5, 10, 20, 50, 100, 500, 1000, 1500, 2000, 2500, 3000, 3500, 4000, 4500, 5000, 5500, 6000, 6500, or more, for example, 1000-10,000 microdevices may be generated, such as 2000-8000, or about 3000-7000.

Defining a plurality of reservoirs in the microdevice structures includes depositing a layer of photoresist onto the first surface of the microdevice structure. Depositing of the photoresist may be carried out in the same manner as described above. The photoresist may be the same photoresist used for fabricating the microdevice structures or a different photoresist. A mask may be positioned over the photoresist layer. The pattern in the mask defined the regions through which light may pass through to the photoresist layer. The pattern in the mask may be any desired pattern depending upon the number, shape and dimensions of the reservoirs to be defined in a microdevice structure.

In certain cases, the plurality of reservoirs present per microdevice include 2 or more, 3 or more, 4 or more, 5 or more, 6 or more, 7 or more, 8 or more, 9 or more, 10 or more, or more. In certain cases, 1-10 reservoirs, or 2-8 reservoirs, or 3-7 reservoirs may be defined in a microdevice structure.

The reservoirs may have any shape, such as, cylindrical, conical, frustoconical, cubical, cuboidal, etc. The volume of the reservoirs may be determined by dimension of the mask region allowing light to pass through to expose the photoresist layer. In addition, the volume of the reservoirs may be determined by the depth to which the polymer layer is removed. The reservoirs may be have a circular shaped opening, the average diameter of the opening may be about 10 $\mu m$, 20 $\mu m$, 30 $\mu m$, 40 $\mu m$, 50 $\mu m$, 60 $\mu m$, 80 $\mu m$, 100 $\mu m$, 120 $\mu m$, 150 $\mu m$, 200 $\mu m$, 250 $\mu m$, or 300 $\mu m$. For example, the average diameter of reservoirs with a circular opening may be in the range of 30 $\mu m$-100 $\mu m$, or about 40 $\mu m$-80 $\mu m$.

Following positioning of a photomask over the microdevice structure, the photoresist may be exposed to light, followed by removal of the exposed photoresist. The regions of the microdevice structures from which the photoresist has been removed may be partially etched to remove a portion of the biocompatible polymer layer. The duration and the intensity of the etching step may be varied to define reservoirs of different depths. For example, the etching process may be carried out for a shorter duration or with a low ion flow rate to define shallow reservoirs while the etching process may be carried out for a longer duration or with a high ion flow rate to define deep reservoirs. In addition, the thickness of the planar layer of biocompatible polymer affects the depth of the reservoir. In general, the average depth of the reservoirs may range from 1 µm-80 µm, 1.5 µm-70 µm, 2 µm-50 µm, 2 µm-30 µm, 3 µm-30 µm, 3.5 µm-20 µm, such as about 1 µm, 2 µm, 3 µm, 4 µm, 5 µm, 6 µm, 7 µm, 8 µm, 9 µm, or 10 µm. The volume of the reservoirs may be range from about $1\times10^{-3}$ nL to about 1 µL, such as about, $5\times10^{-3}$ nL to about 0.1 µL, or about $1\times10^{-2}$ nL to about 50 nL, or about $1\times10^{-2}$ nL to about $5\times10^{-1}$ nL, for example. Accordingly, the microdevices may include a plurality of reservoirs where the reservoirs are open on the first surface due to the removal of the polymer layer by etching and are closed on the second surface due to the presence of the polymer layer. As such, a bioactive agent deposited into the reservoirs may exit through the opening on the first surface of the microdevice.

In certain cases, an adhesion molecule may be attached to the first surface of the microdevice to facilitate the attachment of the first surface of the microdevice to the cells of a target tissue. Accordingly, the microdevices include reservoirs comprising a single opening, wherein the opening is located on the first surface of the microdevices, which first surface may be the cell contacting surface. Exemplary adhesion molecules, that facilitate adhesion of the microdevice to the cells of a target tissue where the bioactive agents loaded into the microdevice need to be delivered, include lectin (e.g., wheat germ agglutinin), polycations (e.g., chitosan, polylysine, and the like), laminin, fibrin, fibronectin, integrin, vitronectin, hyaluronic acid, elastin, vitronectin, proteoglycans, glycoproteins, glycosaminoglycans, collagen, gelatin, and the like. The adhesion molecule may be attached covalently or non-covalently to the first surface of the microdevice. The method may include attaching an adhesion molecule to the first surface of the microdevice after defining the microdevice structure and before defining the reservoirs. In certain cases, the method may include attaching an adhesion molecule to the first surface of the microdevice after introducing the plurality of reservoirs in the microdevice structure. The cell adhesion molecule may be attached covalently to the first surface of the microdevice using a standard chemistry, which does not affect the integrity or stability of the polymer layer.

In certain embodiments, the target tissue may be a mucosal tissue of a patient. For example, the target tissue may be gastrointestinal tissue, for example, esophagus, stomach, small intestine, large intestine. In other embodiments, the target tissue may be mucosal tissue in mouth, such as, epithelial cell lining of the mouth. The microdevices described herein may be administered to a patient in need thereof by a number of routes of administration, including but not limited to, oral, sublingual, ocular, intra-vaginal, intra-rectal.

As described above, the bioactive agent(s) may be deposited into the reservoirs in conjunction with a prepolymer. The preolymer may be polymerized by a variety of techniques, such as, exposure to light, heating, drying, and the like. In certain embodiments, the prepolymer polymerizes upon exposure to light, such as, UV light. In these embodiments, a solution of a bioactive agent and a prepolymer deposited into a plurality of reservoirs of a microdevice(s) may be polymerized by exposure to light. In certain embodiments, only the reservoirs are exposed to light by using an appropriately patterned mask. In certain cases, a mask similar to the mask used for creating the reservoirs may be used for exposing the reservoirs to light.

In certain cases, a first solution containing a first bioactive agent and a polymer present in a first reservoir may be polymerized by exposing only the first reservoir to light using a mask patterned to allow light to pass through to only the first reservoir. Any unpolymerized first solution may be removed. The method may further comprise, depositing a second bioactive agent into the microdevice. The depositing step may result in filling of any empty reservoirs with the second bioactive agent. As noted above, the second bioactive agent may be deposited in form of a second solution comprising the second bioactive agent and the same polymer used with the first bioactive agent or a different prepolymer. The method further comprises exposing only the second reservoir to light thereby polymerizing the second bioactive agent in the second reservoir. Any unpolymerized second solution may then be removed. The steps of depositing a solution containing a bioactive agent and a prepolymer, polymerizing the solution in a particular reservoir by using a mask and light, and removing unpolymerized solution may be repeated to fill different reservoirs with different bioactive agents.

In further embodiments, the release kinetics of the bioactive agents that is eluted from the microdevice may be modulated by using an appropriate prepolymer or a combination of prepolymers and cross-linkers, modulating the concentration of the prepolymers and/or cross-linkers. As used herein, the term "prepolymer" refers to a polymer that is not yet polymerized into a semi-solid or solid state. A synthetic or natural polymer can be used as a polymer and may be combined with the bioactive agent prior to or at the same time microdevices are loaded with the bioactive agent. Suitable synthetic and natural polymers include, but are not limited to, biodegradable or bioerodible polymers, such as poly(DL-lactide-co-glycolide) (PLGA), poly(DL-lactide-co-ε-caprolactone) (DLPLCL), or poly(ε-caprolactone) (PCL), collagen, gelatin, agarose, and other natural biodegradable materials. In certain embodiments, the concentration of the polymer may be decreased or increased to achieve a higher or lower release kinetic for a bioactive agent. In certain cases, the release kinetics may be modulated by controlling the ratio of a cross linker to a monomer that react to form a polymerized gel. For example, poly(ethylene glycol)dimethacrylate (PEGDMA) may be used to cross-link a monomer such as monomethyl methacyrlate. The ratio of the crosslinker to monomer may be decreased resulting in a less dense polymer through which the bioactive agent is released at a higher rate upon swelling of the polymer. Increasing the ratio of the crosslinker to monomer may result in a dense polymer through which the bioactive agent is released at a slower rate upon swelling of the polymer. A similar effect can also be obtained with the use of different molecular weight (length of the chain) monomers or cross-linkers. In certain embodiments, a first bioactive agent may be polymerized with a first polymer and a second bioactive agent may be polymerized with a second polymer, where the first and second polymers release the bioactive agents at different rates.

In general, the microdevice will elute the bioactive agent to the surrounding tissue upon placement of the microdevice in a patient for a period ranging from about 2 minutes to about 3 months or more, including 5 minutes to about 14 weeks, such as 10 minutes, 30 minutes, 60 minutes, 100 minutes, 130 minutes, 200 minutes, about 6 hours, about 12 hours, about 24 hours, 72 hours, about 3 days, about 7 days, about 2 weeks, about 3 weeks, about 4 weeks, about 6 weeks, about 8 weeks, about 12 weeks, or more. As noted above, a first bioactive agent may be released from the first reservoir and a second bioactive agent may be released from a second reservoir over a similar period of time or over different periods of time.

In general, the subject method produces microdevices that are substantially planar, and provide for release of the bioactive agent(s) deposited in the reservoirs of the microdevice from the first surface of the microdevice. As such, the release of the bioactive agents is substantially in a single direction in contrast to bioactive agents release from a capsule, tablet, or microsphere. In addition, in certain embodiments, the microdevice includes a cell adhesion molecule that mediates attachment of the first surface of the microdevice to the surface of a target tissue, such as, to epithelial cells of a mucosal lining of the gastrointestinal tract. The combination of attachment of the first surface of the microdevice to the target tissue and release of the bioactive agent from the first surface of the microdevice provides a localized release of the bioactive agent in close proximity to the target tissue, thereby providing a higher effective concentration of bioactive agent available for uptake by the cells. As such, the microdevice lowers the amount of bioactive agent that may be required to treat a condition. In addition, the attachment of the microdevice to the target tissue may increase the residence time of the microdevice near the target tissue. For example, attachment of the microdevice to the epithelial lining of the gastrointestinal tract increases its residence time in the gastrointestinal tract as the attached microdevice may be better able to resistant peristaltic motion of the gastrointestinal tract. Moreover, the microdevice may be sized to increase the surface area available to attach to the cells of the target tissue while simultaneously being resistant to the shear stress that may be present in the target tissue.

In general, the openings of the reservoirs of the microdevice structures are located on the first surface of the microdevice facilitating simultaneous release of the bioactive agents present in the reservoirs. This feature of the microdevices may be especially useful for simultaneous release of different bioactive agents.

In certain embodiments, the planar geometry of the microdevice leads to an improvement in the delivery of a bioactive agent, included in a reservoir of the microdevice, to the target tissue. In certain embodiments, the size of the microdevice leads to an improvement in the delivery of a bioactive agent, included in a reservoir of the microdevice, to the target tissue. In certain embodiments, the planar geometry and the size of the microdevice leads to an improvement in the delivery of a bioactive agent, included in a reservoir of the microdevice, to the target tissue. Without being bound to a particular theory, it is hypothesized that the microdevice described herein is capable of binding to the target tissue, for example, epithelial cell lining of intestinal wall, and mechanically restructure cell to cell adhesion of the cells. This restructuring of cell to cell adhesion by, for example, modulation of the tight junctions between the epithelial cells of intestinal wall, may result in increased permeability of the epithelial cell lining and thus may result increased delivery of the bioactive agent to the target tissue.

The bioactive agents may be in a purified form, partially purified form, recombinant form, or any other form appropriate for inclusion in the microdevices. In general, the bioactive agents are free of impurities and contaminants. Exemplary bioactive agents that may be incorporated in the microdevices are sugars, carbohydrates, peptides, nucleic acids, aptamers, small molecules, large molecules, vitamins; inorganic molecules, organic molecules, proteins, co-factors for protein synthesis, antibody therapies, such as Herceptin®, Rituxan®, Myllotarg®, and Erbitux®; hormones, enzymes such as collagenase, peptidases, and oxidases; antitumor agents and chemotherapeutics such as cis-platinum, ifosfamide, methotrexate, and doxorubicin hydrochloride; immuno-suppressants; permeation enhancers such as fatty acid esters including laureate, myristate, and stearate monoesters of polyethylene glycol; bisphosphonates such as alendronate, clodronate, etidronate, ibandronate, (3-amino-1-hydroxypropylidene)-1,1-bisphosphonate (APD), dichloromethylene bisphosphonate, aminobisphosphonatezolendronate, and pamidronate; pain killers and anti-inflammatories such as non-steroidal anti-inflammatory drugs (NSAID) like ketorolac tromethamine, lidocaine hydrochloride, bipivacaine hydrochloride, and ibuprofen; antibiotics and antiretroviral drugs such as tetracycline, vancomycin, cephalosporin, erythromycin, bacitracin, neomycin, penicillin, polymycin B, biomycin, chloromycetin, streptomycin, cefazolin, ampicillin, azactam, tobramycin, clindamycin, gentamicin, and aminoglycocides such as tobramycin and gentamicin; and salts such as strontium salt, fluoride salt, magnesium salt, and sodium salt.

Examples of antimicrobial agents include, but are not limited to, tobramycin, amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, and tioconazole.

Antiangiogenic agents include, but are not limited to, interferon-α, COX-2 inhibitors, integrin antagonists, angiostatin, endostatin, thrombospondin-1, vitaxin, celecoxib, rofecoxib, JTE-522, EMD-121974, and D-2163, FGFR kinase inhibitors, EGFR kinase inhibitors, VEGFR kinase inhibitors, matrix metalloproteinase inhibitors, marmiastat, prinomastat, BMS275291, BAY12-9566, neovastat, rhuMAb VEGF, SU5416, SU6668, ZD6474, CP-547, CP-632, ZD4190, thalidomide and thalidomide analoges, sqalamine, celecoxib, ZD6126, TNP-470, and other angiogenesis inhibitor drugs.

In some embodiments, the bioactive agent is a small molecule, such as but not limited to an anti-inflammatory drug, an immunosuppressant drug, a vitamin, micronutrient or antioxidant, an antibacterial drug (e.g., vancomycin or cephazolin), an anti-viral drug (e.g., gancyclovir, acyclovir or foscarnet), an anti-fungal drug (e.g., amphotericin B, fluconazole or voriconazole) or an anti-cancer drug (e.g., cyclophosphamide or melphalan). In certain embodiments, the small molecule is a vitamin, micronutrient or antioxidant, such as but not limited to, vitamin A, vitamin C, vitamin E, zinc, copper, lutein or zeaxanthin. In certain embodiments, the small molecule is an immunosuppressant drug, such as but not limited to, cyclosporine, methotrexate or azathioprine. In certain embodiments, the small molecule is an anti-inflammatory drug, such as but not limited to, a corticosteroid (e.g., triamcinolone acetonide or dexamethasone) or a non-steroidal drug (e.g., ketorolac or diclofenac).

In certain embodiments, the large molecule drug is an immunosuppressant drug, such as but not limited to, etanercept, infliximab or daclizumab. In certain embodiments, the large molecule drug is a neuromuscular blocker drug, such as but not limited to, botulinum toxin A. In certain embodiments, the large molecule drug is a complement inhibitor, such as but not limited to, an anti-C3 compound.

In certain embodiments, the bioactive agent may be Mesalazine, also known as Mesalamine, or 5-aminosalicylic acid (5-ASA), prednisone, TNF inhibitor, azathioprine (Imuran), methotrexate, or 6-mercaptopurine, aminosalicylate anti-inflammatory drugs, corticosteroids, azathioprine, mercaptopurine, methotrexate, infliximab, adalimumab, certolizumab, natalizumab, and hydrocortisone, statins, e.g., atorvastatin, such as atorvastatin calcium, anti-psychotic drugs, e.g., olanzapine.

In certain cases, the bioactive agent may be combined with a pharmaceutically acceptable additive before or after placement of the bioactive agent on a layer of the subject device. The term "pharmaceutically acceptable additive" refers to preservatives, antioxidants, emulsifiers, dyes and excipients known or used in the field of drug formulation and that do not unduly interfere with the effectiveness of the biological activity of the active agent, and that is sufficiently non-toxic to the patient. For example, the bioactive agent may be formulated with inert fillers, anti-irritants, gelling agents, stabilizers, surfactant, emollients, coloring agents, preservatives, or buffering agents, as are known in the art. The term "excipients" is conventionally known to mean carriers, diluents and/or vehicles used in formulating drug compositions effective for the desired use.

The microdevice may be configured to deliver any therapeutic of choice. For example, the microdevice may be configured to deliver therapeutics that are delivered orally, such as, in the form of pills, tablets, capsules, solutions, emulsions, and the like. The microdevice may be suitable for treatment for a variety of conditions. For example, the microdevice may be administered to patients diagnosed with inflammatory bowel disorder, irritable bowel syndrome, Crohn's disease, cancer, such as, intestinal cancer, Ulcerative colitis, etc.

The methods and devices disclosed herein can be used for both human clinical medicine and veterinary applications. Thus, the subject or patient to whom the device is administered can be a human or, in the case of veterinary applications, can be a laboratory, agricultural, domestic, or wild animal. The subject devices and methods can be applied to animals including, but not limited to, humans, laboratory animals such as monkeys and chimpanzees, domestic animals such as dogs and cats, agricultural animals such as cows, horses, pigs, sheep, goats, and wild animals in captivity such as bears, pandas, lions, tigers, leopards, elephants, zebras, giraffes, gorillas, dolphins, and whales.

The dosage of the microdevices required to treat a condition may be determined empirically or experimentally by a trained physician, and may depend on a number of factors, such as, route of administration, severity of the condition, amount of bioactive agent loaded per microdevice, etc. Utilizing ordinary skill, the competent clinician will be able to optimize the dosage of a particular therapeutic in the course of routine clinical trials.

Microdevices

As noted above, a substantially planar microdevice comprising a plurality of reservoirs, wherein the planar device is provided. The substantially planar microdevice comprising a plurality of reservoirs is prepared by a method comprising fabricating a planar layer of a biocompatible polymer on a substrate; defining a microdevice structure in the planar layer using successive deposition of photoresist layer, light exposure, and etching; an introducing a plurality of reservoirs in the microdevice structure using successive deposition of photoresist layer, light exposure, and partial etching, thereby producing a planar microdevice comprising a plurality of reservoirs, wherein the plurality of reservoirs are open at a first surface of the microdevice and are closed at the second surface of the microdevice.

In certain embodiments, the plurality of reservoirs comprise a bioactive agent, the method further comprising depositing a solution comprising the bioactive agent and a prepolymer into the plurality of reservoirs and polymerizing the solution.

In some cases, a first reservoir of the plurality of reservoirs comprises a first bioactive agent and second reservoir of the plurality of reservoirs comprises a second bioactive agent, the method further comprising depositing a first solution comprising the first bioactive agent into the plurality of reservoirs; polymerizing the first solution only in the first reservoir; removing unpolymerized first solution; depositing a second solution comprising the second bioactive agent into the plurality of reservoirs; polymerizing the second solution only in the second reservoir.

In certain cases, the microdevice comprises an adhesion molecule attached to the first surface to facilitate adhesion of the first surface of the microdevice to cells of a target tissue.

The biocompatible polymer may be poly(DL-lactide-co-glycolide) (PLGA), poly(DL-lactide-co-$\epsilon$-caprolactone) (DLPLCL), poly($\epsilon$-caprolactone) (PCL), collogen, gelatin, agarose, poly(methyl methacrylate), galatin/$\epsilon$-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In certain cases, the biocompatible polymer may be poly(methyl methacrylate) or a derivative thereof. In other cases, the biocompatible polymer may be poly($\epsilon$-caprolactone) (PCL) or a derivative thereof.

The microdevice may have an average thickness of about 5 µm to about 100 µm and wherein fabricating the substantially planar layer comprises depositing the biocompatible polymer at an average thickness of about 5 µm to about 100 µm.

In certain cases, the microdevice may be disc-shaped. The microdevice may have an average diameter of about 50 µm-1000 µm.

In certain embodiments, the plurality of reservoirs may different depths, and/or different volumes, and/or different diameters.

In certain embodiments, the cell adhesion molecule may be lectin, chitosan, laminin, fibrin, fibronectin, proteoglycans, glycoproteins, glycosaminoglycan, or a combination thereof.

Microdevices having features similar to the microdevices disclosed herein are described in U.S. Ser. No. 12/530,015 filed on Nov. 16, 2010, which is incorporated herein by reference in its entirety.

Kits

Kits for use in connection with the subject invention are also provided. The above described microdevice comprising a plurality of reservoirs may be provided in kits, with suitable instructions in order to conduct the methods, such as, depositing bioactive agents into the reservoirs, as described above. Instructions (e.g., written, tape, VCR, CD-ROM, etc.) for carrying out the methods may be included in the kit. The kit can also contain, depending on the particular method, other packaged reagents and materials (i.e. buffers and the like).

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or sub-packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the Examples below.

Fabrication of PMMA Microdevices

Materials for microdevice fabrication. All chemicals were purchased from Sigma Aldrich and used as received, unless noted otherwise. Concentrated sulfuric acid, 30% hydrogen peroxide, acetone, methanol, and isopropanol were used for standard RCA pre-cleaning of the wafers. The device material poly(methyl methacrylate); (PMMA) of molecular mass 950,000 suspended in 11% anisole, Shipley 1818 positive photoresist, microposit 351 developer, and 1112A photoresist remover were purchased from Microchem. Positive masks for fabricating the device body (200 µm circles) and its reservoirs (three 60 µm circles inside the 200 µm bigger body circle) were obtained from CAD art services (Badon, Oreg.). The three 60 µm circles were placed on the corners of an equilateral triangle equidistant from the center of the 200 µm circle.

Microfabrication process. Photolithography and reactive ion etching were used to create 200×8 µm cylindrical PMMA microdevices with three 60×5 µm cylindrical reservoirs over 3-inch silicon wafers. Each wafer was cleaned in piranha solution (3:1::$H_2SO_4$:$H_2O_2$) for 20 min, and rinsed with deionized water thrice. Wafers were then rinsed with acetone, methanol, isopropanol, and baked at 100° C. for 2 min to remove all impurities. FIG. 1, panel A shows the scheme of steps involved in the microfabrication process. The wafers were spin coated twice with PMMA (1400 rpm, 30 s) using a Headway Research PW101 spinner (Garland) to get the microdevice body layer. Baking was done before and after the second coat (110° C., 1 min) on a vented hot plate to remove solvents from the PMMA layer. After 2 min of cooling, the wafers were spin coated with positive photoresist (5000 rpm, 30 s) and pre-baked (110° C., 1 min). The cooled wafers were then exposed to a 405 nm UV light of a mercury lamp using a Karl Suss MJB3 mask aligner holding the positive photomask that defines the 200 µm microdevice body at 16 mW/cm$^2$ for 20 s. The photoresist was developed for 75 s in a 1:3 solution of 351 microposit developer to de-ionized (DI) water. The wafers were then rinsed in a DI water cascade, blown dry with nitrogen, and post-baked (110° C., 1 min) The exposed PMMA was dry etched away using a Surface Technology Systems PE1000 AC Plasma Source Reactive ion etcher (RIE; PETS Inc.) at 20% oxygen flow, 30 mTorr pressure, and 450 W power (75%) for 10 minutes. After etching any residual photoresist was removed using a 1112A photoresist remover for 1 min, followed by water, isopropanol rinse, and blown dry with nitrogen.

Once the device body was defined, a second photolithography step was performed to define the microdevice reservoirs. The wafers were spin coated with positive photoresist (5000 rpm, 30 s), pre-baked (110° C., 1 min), and again exposed to UV light using the mask aligner through the second photomask designed to define the three 60 µm microdevice reservoirs. The reservoirs were aligned to the microdevice body using front side alignment techniques on the same mask aligner. Following exposure, the wafers were developed as before using the 351 developer-DI water mixture, rinsed in a DI cascade, nitrogen dried, and post-baked. The unmasked reservoir defining areas were reactive ion etched as before for 8 minutes. The depth of the reservoirs can be controlled by the etching time, but for this work, 5 µm deep reservoirs were obtained. Any residual resist was removed by using 1112A resist remover solution. Characterization of the microdevice dimensions was done using an Ambios Technology XP-2 Stylus Profiler at a scan speed of 0.05 mm/s, a length of 500 µm, and a stylus force of 0.8 mg, while a Novel X my-SEM (Lafayette, Calif.) scanning electron microscope was used to visualize the microdevices.

PMMA-protein Binding Chemistry

Surface aminolysis. The bioadhesive property to the PMMA microdevices is provided by binding targeting proteins to their surface Amine groups were introduced to the PMMA microdevices using N-lithioethylenediamine. Briefly, N-lithioethylenediamine was synthesized by purging 19.8 mL of ethylenediamine with nitrogen for 30 min 400 µl of butyllithium in 2 M cyclohexane was then added to ethylenediamine and the reaction was allowed to proceed under nitrogen atmosphere for 3 hr under constant stirring.

The PMMA microdevice containing wafers were surface modified to include amines only on the sides containing the reservoirs. The wafers were rinsed in DI water, blown dry with nitrogen, and placed on a petri dish that was supplied with nitrogen. After 2 min of nitrogen purging, 500 µl of N-lithioethylenediamine was added to the wafers and evenly applied to coat all microdevices. After 3 min, the wafers were taken out and immersed in DI water to stop aminolysis and eventual release of pH responsive PMMA microdevices from the wafer. After gentle washing in DI water, the wafers were blown dry with nitrogen.

Surface immobilization of protein. The amines were conjugated to model protein tomato lectin (Fluorescein isothiocyanate (FITC)-labeled) using 1-Ethyl-3-(3-dimethylaminopropyl)carbodiimide (EDC; Invitrogen) and N-Hydroxisuccinimide (NHS; Invitrogen). Briefly, to 600 µl of 1 mg/mL model protein in MES buffer (pH 5.5), 13 µl of 100 mM EDC and 13 µl of 200 mM NHS were added and allowed to react for 20 min. Once, the carboxylic acid groups of the proteins were modified into a stable EDC-NHS ester, the reaction was stopped by adding 0.8 µl of 14 M β-mercaptoethanol. After a mM, the pH of the protein mixture was raised to 7.4 by adding sodium bicarbonate and immediately applied to the amine functionalized PMMA microdevice wafers. The binding of the amine groups of PMMA with the modified carboxylic acid groups of the protein was allowed to take place for 4 hr, after which, the wafers were extensively rinsed with DI water to remove any non-covalently bound protein.

Drug loading of microdevices. Single or multiple drugs are loaded to the microdevice reservoirs using photolithography. Briefly, hydrogel-drug prepolymer solutions were prepared by mixing 2 mL of crosslinker poly(ethylene glycol) dimethacrylate (PEGDMA; 750 mol wt) with 300 µl of 60 mg/mL photoinitiator dimethyl acetophenone (DMPA) in monomer monomethyl methacrylate (MMA), and 200 µl of 3 mg/mL model fluorophore-drug in PBS. The model fluorophore-drug was dissolved in PBS via sonication prior to mixing with the crosslinker-monomer solution. The different fluorophore-drugs used were fluorescently labeled bovine serum albumins (BSA)—fluorescein isothiocyanate-BSA (FITC-BSA; excitation (ex): 494 nm; emission (em): 520 nm), Texas red-BSA (ex: 596 nm; em: 615 nm), and 2,4-dinitrophenylated-BSA (DNP-BSA; ex: 360 nm; em: 385 nm). Upon mixing all ingredients for hydrogel prepolymer solution, the mixture was sonicated for 30 min to ensure equal distribution of initiator and drug.

Figure 2:
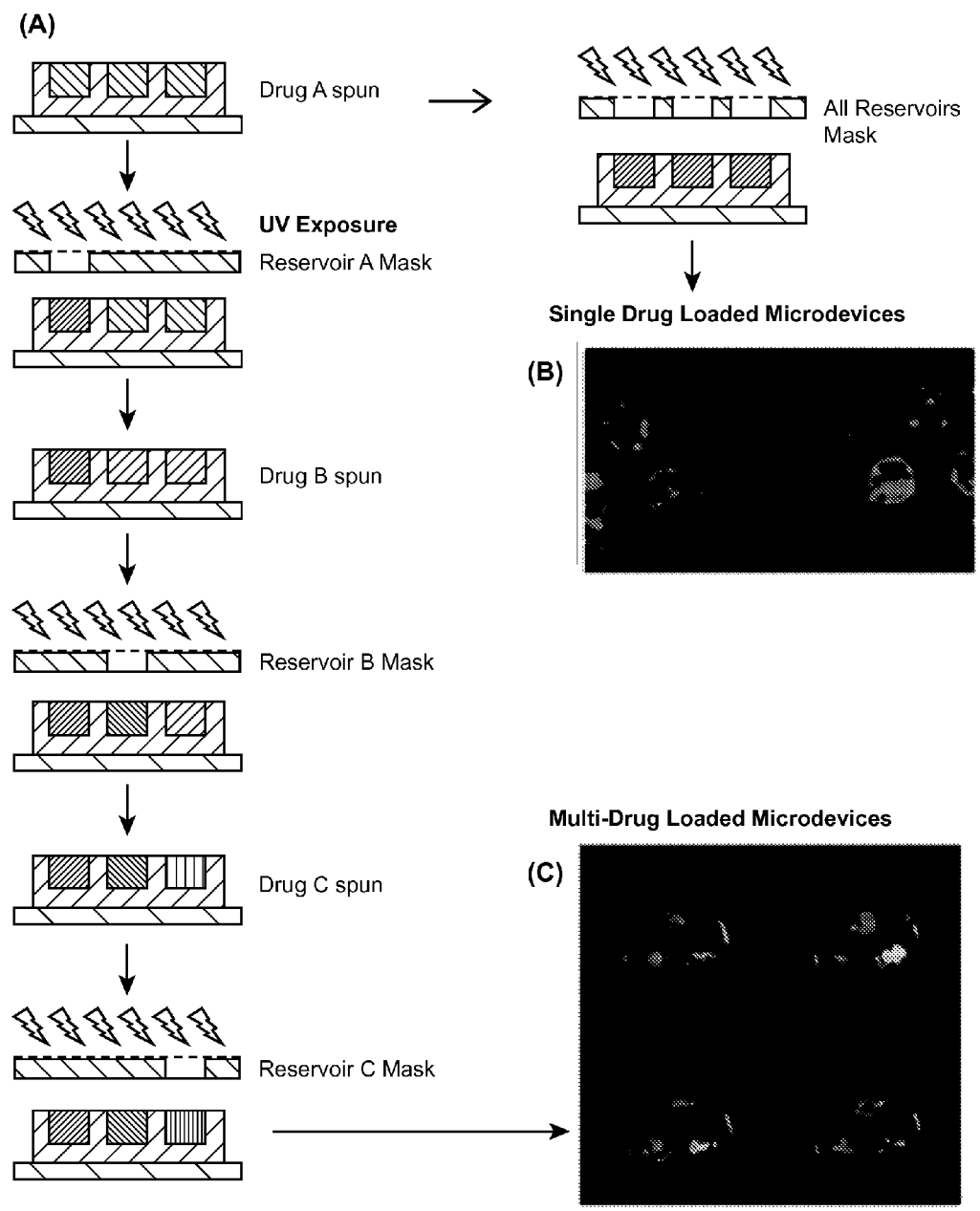
FIG. 2, Panel A, shows a schematic of process for fabricating single or multi-drug loaded microdevices.

For single drug loaded microdevices, the prefabricated wafers were spin coated (3000 rpm, 30 s) with 300 µl of the respective single drug prepolymer solution and exposed to UV light for 90 s using the mask aligner (FIG. 2, Panel A). The photomask used for single drug loading in all three reservoirs is a negative photomask designed to allow light to pass through all three 60 µm reservoirs for photopolymerization of the prepolymer solution into a drug encompassing hydrogel matrix. Development was done using DI water for 30 s and blown dry using nitrogen. For loading of multiple drugs individually in their respective reservoirs, a series of spin coating, alignment, exposure, development, and drying was done using three different negative masks, each allowing light to pass through only one of the reservoirs for photopolymerization (FIG. 2, Panel A). Also, a similar multi-drug loaded wafer was obtained by varying the cross-linking ratio of the prepolymer solution. The crosslinking ratios (PEGDMA:MMA) were 15:85, 30:70, and 45:55 for Texas red-BSA, FITC-BSA, and DNP-BSA, respectively.

Fluorescent microscopy of the protein conjugated and drug loaded devices was done using an Olympus BX60 microscope (Mellville, N.Y.).

In vitro drug permeation studies. The drug loaded microdevices were released within 2 min from the wafers using 8 M potassium hydroxide (KOH) solution that was preheated to 40° C. The released microdevices being less dense than water was ultracentrifuged (30 kDa Amicon ultra centrifugal filters) and washed with PBS twice for release and permeation studies. Human colorectal adenocarcinoma epithelial cells (caco-2 ATCC) were grown to confluency (transepithelial electrical resistance plateau at 900-1000Ω) on 50% collagen-ethanol (Type 1, Becton Dickinson, Franklin Lakes, N.J.) treated 24-well Transwell® inserts. The caco-2 cells were maintained in Modified Eagle's Media (MEM) with 20% fetal bovine serum (Invitrogen), 2 mM L-glutamine, 1.5 g/L sodium bicarbonate, 2.5 g/L glucose, 10 mM HEPES buffer, 1.0 mM sodium pyruvate, and 1 mg/mL penicillin/streptomycin for 5 days or more prior to seeding. 500 µl of the microdevice solution containing about 1800 devices was added to the Transwell® insert. Discrete time (20 min) samples were taken from both the upper and lower chamber of the Transwell® for the different drug loaded systems and observed for fluorescence using a Packard Fluorocount Microplate Fluorometer (Meriden, Conn.).

Bioadhesive displacement studies. Caco-2 monolayers were grown to confluency on 6 well plates under standard conditions. About 100 microdevices per sample (with and without lectin and/or hydrogel) were incubated on the monolayer surface using PBS for 30 min at 37° C. The wells were then visualized using the microscope. The wells were then displaced five times in a controlled vertical fashion with PBS. The initial view field that was imaged before displacement was imaged again and the microdevices were traced in a MS Word grid. Devices that were within 80% of their initial area were considered still stationary and bioadhesive. Those microdevices that were outside the initial 80% area were considered to be displaced.

Example 1

Fabrication of Drug Loaded Microdevices

A series of photolithographic steps and reactive ion etching was used to fabricate 5600 microdevices per silicon wafer. Herein, circular shaped microdevices with three drug reservoirs were fabricated from PMMA with dimensions that would allow for in vivo transit through the mammalian gastrointestinal wall (thickness of about ten microns, and the length of the maximum dimension being 200 µm). Though it is possible to fabricate a multitude of devices of varying dimensions and shapes, herein as shown in the SEM image (FIG. 1, Panel B), a circular 200 µm device with three 60 µm reservoirs was maintained as the prototype. FIG. 1, Panel C shows the thickness profile of the device along the dotted line using a profilometer. The prototype device had a body thickness of about 7.5 µm, while the reservoirs were 5 µm deep. The thickness of the devices is chosen small enough to reduce the shear forces, per mass, experienced by the microdevice sides to flow conditions that can dislodge the device and disrupt therapeutic release and eventual permeation. The device body thickness limits the depth to which the reservoirs can be etched. In other words, the device thickness governs the volume of drug that can be loaded in a reservoir. By varying the spin speed of PMMA (1000-5000 rpm), the number of PMMA layers (1-3 layers), and baking (with or without a bake step in between layers), the thickness of the devices were varied from 3-12 µm. Any further layering had no significant effect on the thickness, while spin rates slower than 1400 rpm produced an edge bead of PMMA on the wafer that varied the aspect ratio significantly. The depth of the reservoirs (3.5-5 µm), and so the drug loading volume was easily adjusted by controlling the etch time or the ion flow rate (RIE power). This control over the drug volume is useful for instances of using expensive and toxic drugs for gastrointestinal (GI) delivery.

FIG. 1, Panel A. Schematic representation of the process of fabricating PMMA microdevices. FIG. 1, Panel B. A scanning electron microscopic image of the fabricated microdevice prototype (200 µm circular device with three 60 µm circular reservoirs). FIG. 1, Panel C. The dimensions of the microdevice, as measured using a profilometer (dotted line). The scale bar represents 100 µm.

The drugs were loaded into the reservoirs as a drug encompassing hydrogel matrix using photolithography (FIG. 2, Panel A). The concentration of the photoinitiator DMPA was optimized to 6% and used to polymerize the entire of the reservoir volume (K. M. Ainslie, T. A. Desai, Lab Chip. 8 (2008), 1864-1878). To confirm the stability of the drug-hydrogel matrix from staying in the reservoirs during flow conditions, the microdevice wafers were agitated (250 rpm) in PBS for three days. No significant loss or removal of the hydrogel from the reservoirs was observed (98.6±0.9% devices remained occupied with hydrogel). From FIG. 2, Panel C, it is observed that a series of spinning and UV exposure in the presence of respective individual reservoir masks leads to the filling of three different drugs to the three reservoirs with ease.

FIG. 2, Panel A. Schematic process overview for fabricating single or multi-drug loaded microdevices using photolithography. FIG. 2, Panel B. A fluorescent micrograph showing the presence of a single model drug (Texas red-BSA) loaded in all three reservoirs of the same microdevice. The drug uniformly filled all three reservoirs. FIG. 2, Panel C. A fluorescent micrograph composite of a multi-drug (Texas red-BSA; red, FITC-BSA; green, DNP-BSA; blue) loaded microdevice as individual drug in separate reservoirs. The white circle highlights the microdevice area.

Example 2

Conjugation of Bioadhesive Proteins to Microdevices

The high surface area of the microdevice (23,000 µm$^2$) can be harnessed to facilitate multi-cell and multi-site attachment of the gastrointestinal mucosa to overcome issues associated with peristalsis and shear flow conditions experienced by current oral delivery systems. Tomato lectin is known to bind specifically to the N-acetylglucosamine moieties present on the epithelial cell lining of the intestinal wall, as modeled in vitro with caco-2 cells (J. Rocca, K Shah, Drug Delivery Technology 2004, 4). Therefore, by introducing bioadhesive tomato lectin the microdevice transit time can be enhanced leading to increased drug retention, permeation, and eventual delivery. Tomato lectin was conjugated to the PMMA microdevice surface using two major steps: (a) the functionalization of PMMA to include amine groups via N-lithioethylene diamine aminolysis, and (b) the formation of amide bonds between the PMMA amines and the protein carboxylic acids using carbodiimide chemistry. The presence of amine functional groups and the ability of carbodiimide chemistry to bind the protein to PMMA surface were indirectly confirmed by probing the surface with fluorophore tagged tomato lectin.

Figure 3:
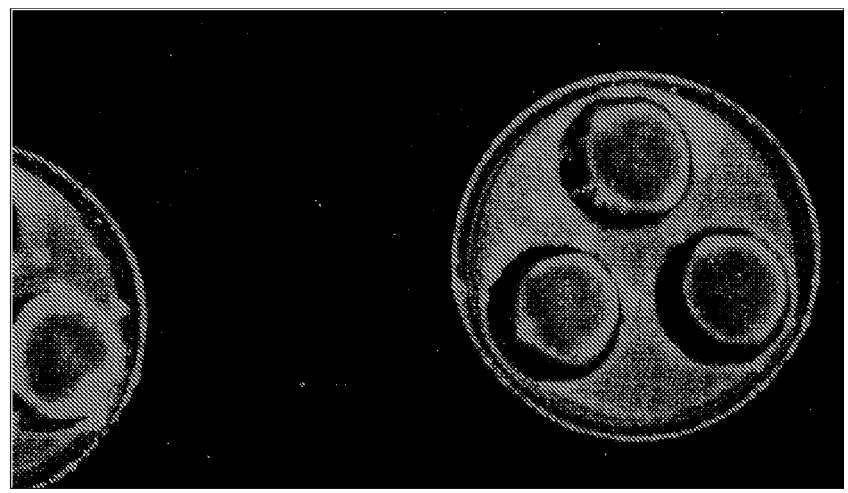
FIG. 3 shows fluorescent micrograph composite confirming conjugation of model fluorophore-lectin to the surface of poly(methyl methacrylate) (PMMA) and showing the loading of model drug.

FIG. 3 shows the fluorescent image of a microdevice that was initially tagged with FITC-tomato lectin and then used to introduce Texas red-BSA to the reservoirs. Since protein conjugation to the microdevices takes place for a time of 4 hr, it is done first prior to drug loading to avoid any drug loss associated with the swelling of hydrogel in the protein solution and eventual release of the drug. It is clear from FIG. 3 that the protein is mostly available on the surface of the PMMA microdevices and is readily available to recognize and bind with intestinal epithelia.

FIG. 3. A fluorescent micrograph composite confirming the conjugation of model fluorophore (FITC)-lectin to the surface of PMMA microdevice (bigger circle) and showing the loading of model drug (three reservoirs within the bigger circle).

The effect of using tomato lectin to introduce bioadhesive properties was confirmed using displacement studies (Table 1). In these displacement studies, microdevices were incubated with and without caco-2 cell monolayer in 6 well plates. The wells were displaced five times in a vertical fashion and device location was observed by comparing the before and after micrographs.

TABLE 1

| Caco-2 monolayer | Microdevice | Drug-hydrogel | Tomato lectin | % Binding |
|---|---|---|---|---|
| − | + | + | + | 0 ± 0 |
| + | + | + | − | 2 ± 1 |
| + | + | − | + | 71 ± 8 |
| + | + | + | + | 59 ± 6 |

Clearly the presence of tomato lectin on the surface of PMMA microdevices enhances the bioadhesive property of the microdevices. Although it may seem that the filling of reservoirs with drug-hydrogel matrix results in a reduction of overall bioadhesive property (59%) as compared that of empty microdevices (71%), this difference may just be from the number of asymmetric devices (conjugated to lectin on one side) that are not facing towards the caco-2 monolayer. It is also observed that a slight percentage of devices as such show binding to the caco-2 monolayer. This number can be increased by using a mucoadhesive material such as chitosan for fabricating the microdevice for enhanced oral drug delivery applications (C. M. Lehr et al., Int. J. Pharm. 78 (1992), 43-48). The bioadhesive property of lectin coated microdevices may prove useful for the targeted treatment of various intestinal diseases such as IBD, IBS, and Crohn's disease.

Example 3

Controlled In Vitro Drug Release from Microdevices

To measure the drug elution kinetics of the various microdevices, release of the different fluorophore tagged BSAs were monitored, in vitro, from hydrogel laden microdevices. BSA has a molecular weight of about 66 kDa (14×4×4 nm$^3$) and is above the gastrointestinal limit of epithelial absorption (20 kDa) (R. Goldie, Ed. C. Page, Elsevier 1994). The volume of a single reservoir is approximately 1.4×10$^{-2}$ nL and therefore a single drug loaded wafer (all three reservoirs loaded with same drug; FIG. 2, Panel B) or a multi-drug loaded wafer (different drug in different reservoir; FIG. 2, Panel C) holds approximately 85 ng of a single drug or 27 ng of each drug respectively. Similar drug loaded hydrogel boluses (hydrogel pellets with no microdevices) were polymerized as control samples and used for in vitro drug release studies. In the presence of a fluid, the hydrogel swells and allows the drug to diffuse out of the polymer matrix. The microdevices were added to the apical side of a caco-2 monolayer that possesses in vivo-like tight-junctions (1-3 nm) and drug concentration was measured in the basal side (K. Kitchens, et al., Pharm. Res. 33 (2006), 2818-2826).

Figure 4:
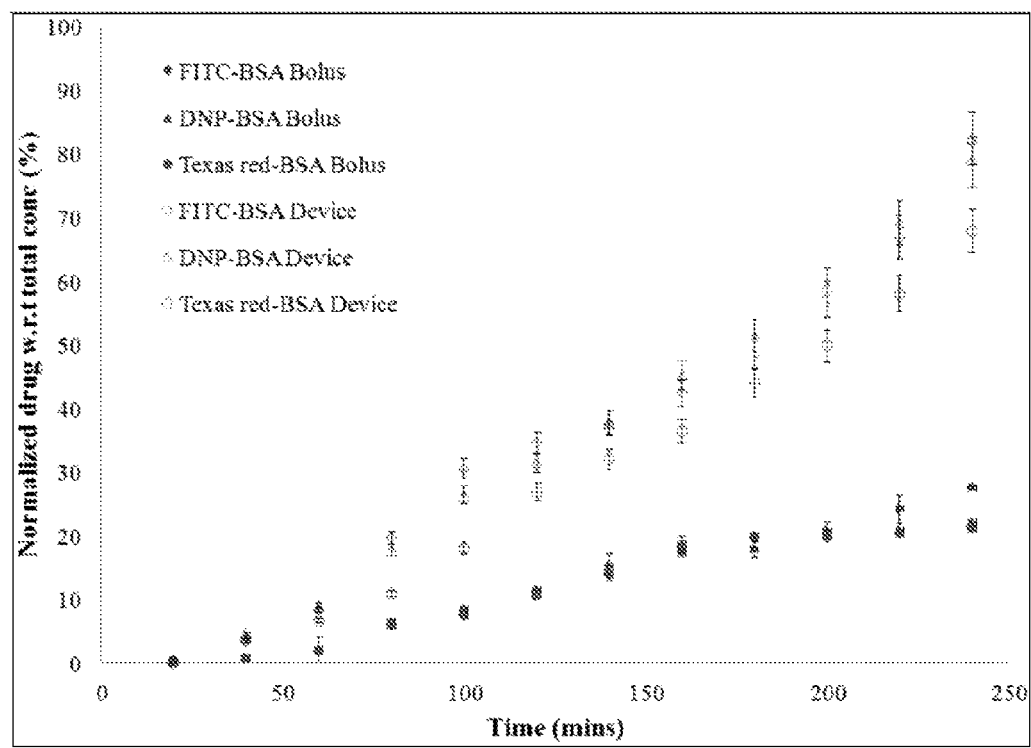
FIG. 4 illustrates permeation of drug loaded in microdevices or hydrogel bolus through Caco-2 epithelial monolayer.

FIG. 4 shows the in vitro release profile of the single drug loaded wafers. Relative to the control (hydrogel bolus) sample, the microdevices show an enhanced permeation of drug across the caco-2 monolayer. This may be attributed to the fact that asymmetric microdevices release drug in a unidirectional way as compared to the hydrogel bolus to provide an increased concentration of drug across the device-cell interface. Similar results have been predicted by others, wherein the transport of high molecular weight proteins is attributed to the increased paracellular transport across the intestinal epithelium in the presence of a bioadhesive microparticle (V. Uskokovic et al., Biomaterials 33 (2012), 1663-1672; K. E. Fischer et al., Nano Lett. 9 (2009), 716-720). This increase in drug permeation caused by the presence of a microdevice is important in the context of being able to improve the oral bioavailability of large molecules.

FIG. 4 shows the enhanced permeation of different single drug loaded microdevices as compared to their respective drug loaded hydrogel bolus (control; without devices) through a caco-2 epithelial monolayer on collagen treated Transwells®. The concentration was normalized with respect to total drug loaded in each microdevice wafer (N=3).

Figure 5:
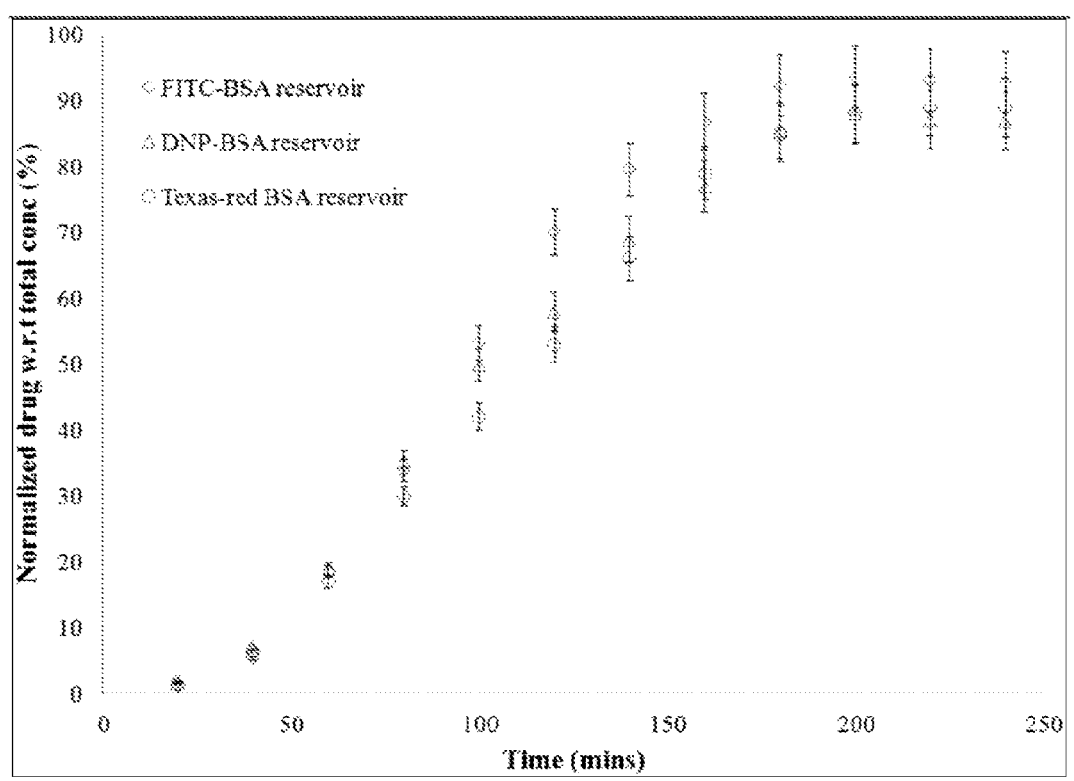
FIG. 5 shows the permeation across Caco-2 epithelial monolayer of different model drugs loaded in the same microdevice.

The effect of using multi-reservoir devices loaded with different individual drug in each reservoir as compared to a previously used single reservoir systems loaded with layers of different drugs was also studied (FIG. 5). In the case of the single reservoir system loaded with multiple drugs loaded in layers of hydrogels, the release of the different drugs depended on the swelling kinetics of the overlaying hydrogel layers (K. M. Ainslie and T. A. Desai, Lab Chip. 8 (2008), 1864-1878). This dependency on the swelling of other hydrogel layers acts as additional barriers for the different drugs to release from the microdevices. It is observed from FIG. 5 that unlike the layered single reservoir systems, the release of all three model fluorophore BSAs from the three reservoir prototype device is independent from each other. This independent release behavior proves useful for combination therapies, wherein multiple drugs are to be delivered at the same time at the same place. All three drugs show linear release up to three hours, after which steady state is reached, which is consistent with the amount of drug loaded in each microdevice per wafer. In addition to the molecular weight and amount of drug loaded, the properties of the drug encompassing polymer matrix can also be modified to control the release kinetics. The polymer can be chosen specifically to release the drug via degradation or in response to external stimuli (pH, temperature, etc.).

FIG. 5 shows the independent permeation of different model drugs from their respective reservoirs of the same microdevice across the caco-2 epithelial monolayer on collagen treated Transwells® (N=3).

The swelling property of the hydrogel matrix in each reservoir was modified to provide different release kinetics by modifying the crosslinking ratio of the hydrogel. Increasing crosslinking ratio of PEGDMA from 15% for Texas red-BSA loaded reservoir to 30% for FITC-BSA reservoir to 45% for DNP-BSA reservoir was used for this study. It is observed from FIG. 6 that Texas red-BSA released faster than FITC-BSA that released faster than DNP-BSA. In other words, the controlled release of different drugs is dependent on the crosslinking ratio of the hydrogel system. This is due to the fact that lower crosslinking ratio (15%) results in the formation of a less tighter/loose mesh network leading to an increased diffusion of the drug, while higher crosslinking ratio (45%) results in the formation of a highly tighter mesh network leading to a decreased diffusion of the drug. A similar effect can also be obtained with the use of different molecular weight (length of the chain) monomers or crosslinkers (H. D. Chirra and J. Z. Hilt, Langmuir 26 (2010), 11249-11257). The use of different polymer systems of varying release and degradation kinetics in each reservoir enables the use of microdevices for timed release of different drugs for effective therapy (A. C. R. Grayson et al., Nat. Mater. 2 (2003), 767-772; A. C. R. Grayson et al., J. Biomed. Mater. Res. Part A. 69A (2004), 502-512). Timed release of drugs from microdevices may enable more effect delivery of therapeutics to different regions of the gut as the device transits through the intestinal tract.

Figure 6:
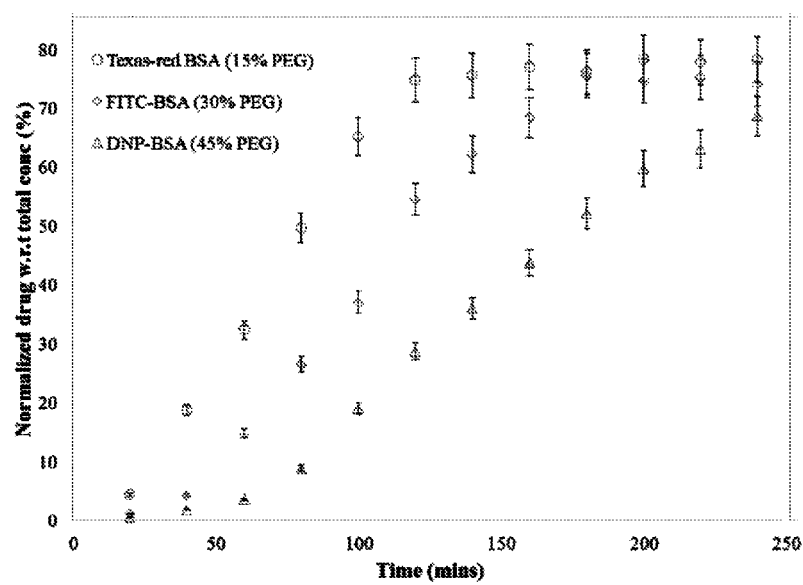
FIG. 6 depicts the controlled release and permeation of different model drugs loaded in the same microdevice but with different crosslinking ratio/amounts of crosslinker.

FIG. 6 shows controlled release and permeation of different model drugs loaded into their respective reservoirs of the same device using different crosslinking ratio/amounts of crosslinker (PEGDMA). Increasing or decreasing the amount of PEG resulted in a slower or faster release of similar molecular weight drug respectively. This proves useful for timed release therapy of various intestinal diseases (N=3).

Example 4

Effect of Microdevices on Gastrointestinal (GI) Bioadhesion

Wild-type C57BL/6 mice (JAX, Bar Harbor, Mass.), aged 8-12 weeks were used in this study. Prior to oral gavage of microdevices, mice were fasted for 24 hours. Sterile 18 ga×38 mm plastic feeding tubes (Instech Solomon, Plymouth Meeting, Pa.) were used to instill 400 ul of PBS solution containing the microdevices (1 wafer of empty devices=5625 devices) with and without GI targeting lectin or a control solution. Mice were then euthanized at the appropriate time points (0, 20, 45, 90, 120 min) according to IACUC guidelines, using intraperitoneal injection of 150-400 mg/Kg of 2,2,2 Tribromoethanol (Sigma, St. Louis, Mo.) at a concentration of 2.25% followed by cervical dislocation. The study protocol (ANS#1692) was approved by and all animal studies were conducted in accordance with the University of California, San Francisco Institutional Animal Care and Use Committee.

Figure 7:
FIG. 7 shows the effect of particle shape and surface functionality on the in vivo bioadhesion of microdevices. Flat microdevices show enhanced bioadhesion than that of spherical particles of same surface area. Further enhancement is provided by the presence of GI epithelia targeting lectin.

Intestines were dissected and divided into glass scintillation vials (Sigma, St. Louis Mo.). Proteinase K (Roche, Indianapolis, Ind.) at a concentration of 1 mg/mL was added and the samples were incubated with gentle rocking at 56° C. overnight. Lysates were passed though 40 uM cell strainers (BD Falcon, Franklin Lakes, N.J.), rinsed with DI water, and collected in a 5 mL water solution prior to quantitation of microdevices. Multiple random 100 µL samples of the washed lysates were added to a glass slide and counted using an optical microscope. The average number of microdevices in the respective sections of the intestine at different time points after gavaging is shown in FIG. 7. A control sample of spherical PMMA microparticles having same surface area as that of flat microdevices was also used for comparison purposes.

The shear experienced by the thin walls of the flat microdevices is less than that of the spherical microparticles of same total surface area. Also, there is an increased contact area in the case of flat microdevices than spherical microparticles. These reasons enhance the chances of a microdevice to stay longer in a given section of the gastrointestine as compared to spherical particles, thereby potentially increasing the residence time of a drug encompassed in microdevices. This should subsequently increase the drugs absorption in the GI and its overall therapeutic bioavailability.

Example 5

Stability of Drug Encompassing Hydrogel Matrix to pH

Figure 8:
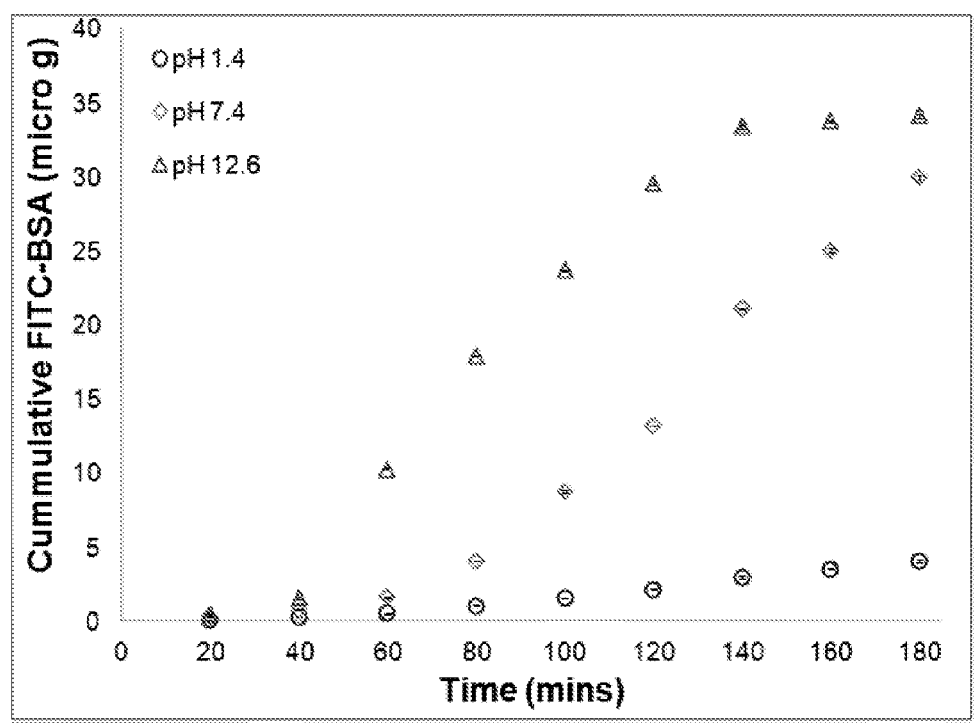
FIG. 8 shows the cumulative release profile of model FITC-BSA from PEGDMA-MMA hydrogel discs at different pH.

The stability of the drug encompassing hydrogel from releasing the drug in the various regions of the intestine was studied using different pH solutions. Briefly, 100 µL of FITC-BSA (37 µg) loaded PEG-MMA solution (used as before in loading microdevice reservoirs) was photopolymerized as hydrogel discs. The 100 µL discs were then individually placed in different pH solutions and the release of FITC-BSA was measured over time using a fluorimeter. FIG. 8 shows the release profile of the drug across different pHs.

Clearly the methacrylate group of the MMA in the hydrogel responds to changes in pH. At pH below pKa, the hydrogel behaves hydrophobic and therefore remains in a compressed state. At this state the diffusion of drug outside of the hydrogel is hindered. At pH above pKa of the hydrogel, they behave hydrophilic and result in swelling of the hydrogel. This opens up the mesh size of the hydrogel, thereby releasing out the model drug at a faster rate via diffusion. Therefore, the chosen PEGDMA-MMA hydrogel system would prove useful in not releasing the drug in the harsh stomach environment (where pH is around 2) but releases the drug faster in the near neutral intestinal and colonic pH.

Example 6

In Vivo Pharmacokinetic Analysis of Delivered Drug 11,000 microdevices/mice (two wafers/mice) were loaded with 17 µg of Acyclovir (Sigma) for this study. Wild-type C57BL/6 mice (JAX, Bar Harbor, Mass.), aged 8-12 weeks, fasted for 24 hours were orally gavaged with Acyclovir loaded microdevices in 500 µL of PBS using sterile 18 ga×38 mm plastic feeding tubes (Instech Solomon, Plymouth Meeting, Pa.). Mice were then euthanized at the appropriate time points (20, 45, 90, 150, 240, and 360 min) according to IACUC guidelines, using intraperitioneal injection of 150-400 mg/Kg of 2,2,2 Tribromoethanol (Sigma, St. Louis, Mo.) at a concentration of 2.25% followed by cervical dislocation. The study protocol (ANS#1692) was approved by and all animal studies were conducted in accordance with the University of California, San Francisco Institutional Animal Care and Use Committee. For serum isolation, blood was obtained by right heart puncture and placed in Z-gel microtubes (Sarstedt, Germany). Samples were then centrifuged at 10000×g in a tabletop centrifuge for 5 minutes at 4° C. Plasma was collected and frozen at −20° C. until further analysis.

For HPLC analysis plasma samples were thawed to room temperature. 7% Perchloric acid was added to an equal volume of plasma and samples were vortex mixed. Precipitated plasma proteins were separated via centrifugation. The supernatant was filtered using a 0.22 µm filter and 100 µL was injected into the column Analysis was carried out using an Agilent 1260 HPLC equipped with a multiple wavelength detector. Separation was performed on a Macherey-Nagel Nucleosil C18 HPLC column equipped with a Nucleosil C18 guard column using a mobile phase comprised of 92% 50 mM octane sulfonate; pH 2.6 and 8% methanol with a flow rate of 1 mL/min. Acyclovir was then detected at 254 nm.

Figure 9:
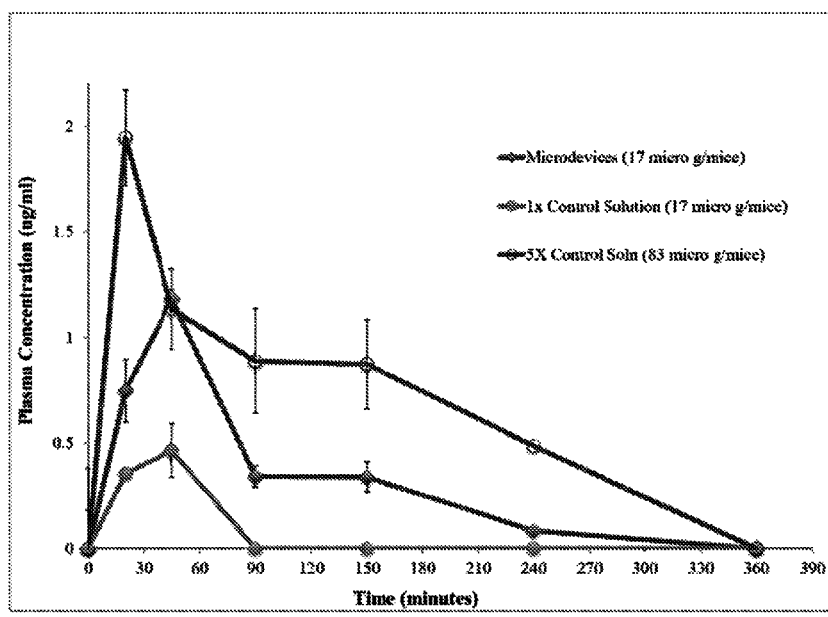
FIG. 9 shows the plasma vs. time curve for Acyclovir released from microdevices compared to Acyclovir solution at same and 5× concentrations.

FIG. 9 shows the pharmacokinetic data of gavaged Acyclovir at various time points. It was observed that the plasma concentration of Acyclovir from microdevices at respective time points is more than that of orally gavaged Acyclovir solution of same concentration. This enhanced bioavailability of Acyclovir in plasma may be attributed to the increased bioadhesion of microdevices (FIG. 7) leading to an increased residency time of drug available for absorption in the small intestinal section of GI. Also, unidirectional release of drug from devices results in an increased local concentration of drug at the device-epithelia interface, thereby resulting in an increased absorption of the drug by the GI. From FIG. 9 it was observed that the bioavailabity of drug achieved from 17 µg of Acyclovir is equivalent to 5×(or 83 µg) of orally gavaged Acyclovir solution. This enhanced bioavailability of drug in spite of low administered dosage of a drug proves useful to alleviate/eliminate systemic side effects associated with administering toxic dosages of drugs.

What is claimed is:

1. A method of preparing a substantially planar microdevice comprising a plurality of reservoirs, the method comprising:
    (i) fabricating a planar layer of a biocompatible polymer on a substrate;
    (ii) defining a microdevice structure in the planar layer using successive steps comprising:
    depositing a first positive photoresist layer on the planar layer;
    exposing the first positive resist layer to irradiation through a first photomask that covers a defined region on the first positive photoresist layer, to render the positive resist layer not covered by the first photomask soluble to a first photoresist developer while shielding the defined region on the first positive resist layer;
    developing the first positive resist layer to remove soluble regions of the first photoresist layer thereby exposing a region of the planar layer under the removed first photoresist layer;
    removing by reactive ion etching the exposed region of the planar layer while the planar layer covered by the defined region of the first positive resist is retained to form the microdevice structure;
    (iii) producing a planar microdevice comprising a plurality of reservoirs using successive steps comprising:
    removing the defined region of the first positive resist from the microdevice structure;
    depositing a second positive resist layer on remainder of the planar layer on the microdevice structure;
    exposing the second positive resist layer to UV light through a second photomask that partially covers the second positive photoresist layer while not covering a plurality of regions on the second positive photoresist layer, to render the plurality of regions on the second positive resist layer not covered by the second photomask soluble to a second photoresist developer;
developing the second positive resist layer to remove the plurality of regions on the second photoresist layer not covered by the second photomask thereby exposing a plurality of regions on the remainder of the planar layer;
removing by partial reactive ion etching the exposed plurality of regions on the remainder of the planar layer wherein the partial reactive ion etching does not etch entire thickness of the planar layer in the plurality of regions, thereby forming a plurality of reservoirs; and
removing second positive resist pattern,
thereby producing the planar microdevice comprising the plurality of reservoirs, wherein the plurality of reservoirs are open at a first surface of the microdevice and are closed at the second surface of the microdevice.

2. The method of claim 1, further comprising depositing a bioactive agent into the plurality of reservoirs.

3. The method of claim 2, wherein the bioactive agent is deposited in the form of a solution comprising the bioactive agent and a prepolymer, wherein the method further comprises polymerizing the solution.

4. The method of claim 1, further comprising:
depositing a first solution comprising a first bioactive agent and a photopolymer into the plurality of reservoirs;
polymerizing the first solution only in a first reservoir of the plurality of reservoirs by exposing the first solution in the first reservoir to light, thereby polymerizing the first solution;
removing unpolymerized first solution from reservoirs not exposed to light;
depositing a second solution comprising a second bioactive agent and a photopolymer into the plurality of reservoirs;
polymerizing the second solution only in a second reservoir of the plurality of reservoirs by exposing the second solution in the second reservoir to light, thereby polymerizing the second solution, thereby providing the first bioactive agent in the first reservoir and a second bioactive agent in the second reservoir.

5. The method of claim 4, wherein the first solution comprises a first prepolymer and the second solution comprises a second prepolymer, wherein the first bioactive agent is released from the first reservoir at a different rate compared to release of the second bioactive agent from the second reservoir.

6. The method of claim 1, further comprising, after defining the microdevice structure, attaching an adhesion molecule to the first surface to facilitate adhesion of the first surface of the microdevice to cells of a target tissue.

7. The method of claim 6, wherein the cell adhesion molecule is lectin, chitosan, laminin, fibrin, fibronectin, proteoglycans, glycoproteins, glycosaminoglycan, or a combination thereof.

8. The method of claim 1, further comprising, after introducing a plurality of reservoirs in the microdevice structure, attaching an adhesion molecule to the first surface to facilitate adhesion of the first surface of the microdevice to cells of a target tissue.

9. The method of claim 1, wherein the biocompatible polymer is poly(DL-lactide-co-glycolide) (PLGA), poly (DL-lactide-co-$\epsilon$-caprolactone) (DLPLCL), poly($\epsilon$-caprolactone) (PCL), collogen, gelatin, agarose, poly(methyl methacrylate),galatin/$\epsilon$-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

10. The method of claim 1, wherein the biocompatible polymer is poly(methyl methacrylate) or a derivative thereof.

11. The method of claim 1, wherein the biocompatible polymer is poly($\epsilon$-caprolactone) (PCL) or a derivative thereof.

12. The method of claim 1, wherein fabricating the substantially planar layer comprises depositing the biocompatible polymer at an average thickness of about 5 µm to about 100 µm.

13. The method of claim 1, wherein the microdevice has an average thickness of about 5 µm to about 100 µm.

14. The method of claim 1, wherein the microdevice is disc-shaped.

15. The method of claim 14, wherein the microdevice has an average diameter of about 50 µm -1000 µm.

16. The method of claim 1, wherein the plurality of reservoirs have different depths.

17. The method of claim 1, wherein the plurality of reservoirs have different volumes.

18. The method of claim 1, wherein the plurality of reservoirs have different diameters.

19. The method of claim 1, further comprising removing the microdevice from the substrate.

* * * * *